(12) United States Patent
Yuki (10) Patent No.: US 7,695,445 B2
(45) Date of Patent: Apr. 13, 2010

(54) THREE-WAY STOPCOCK, AND LIQUID TRANSFUSION CIRCUIT OR BLOOD TRANSFUSION CIRCUIT EITHER USING THE THREE-WAY STOPCOCK

(75) Inventor: Takehiko Yuki, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 909 days.

(21) Appl. No.: 10/494,954

(22) PCT Filed: Nov. 11, 2002

(86) PCT No.: PCT/JP02/11715

§ 371 (c)(1),
(2), (4) Date: May 7, 2004

(87) PCT Pub. No.: WO03/041788

PCT Pub. Date: May 22, 2003

(65) Prior Publication Data

US 2005/0043668 A1 Feb. 24, 2005

(30) Foreign Application Priority Data

Nov. 14, 2001 (JP) .............................. 2001-348142

(51) Int. Cl.
*A61M 37/00* (2006.01)
*A61M 5/178* (2006.01)
*A61M 5/315* (2006.01)
*A01G 25/16* (2006.01)
*F16K 5/00* (2006.01)

(52) U.S. Cl. .................. 604/4.01; 604/6.1; 604/167.05; 604/236; 604/248; 604/288.03; 137/625; 251/309

(58) Field of Classification Search .................. 604/32, 604/99.02, 167.05, 246, 1, 9, 6.16, 99.04, 604/167.03, 236, 247, 248, 288.03; 128/214 B, 128/214 R, 274, DIG. 26; 137/556, 556.6, 137/595, 599, 625.11, 625.19, 625.23, 625.4, 137/625.41, 625.42, 625.46, 625.47, 626, 137/862; 251/188, 297, 309, 368, 904; 600/248, 600/288.03
See application file for complete search history.

(56) References Cited

U.S. PATENT DOCUMENTS 3,048,192 A * 8/1962 Murphy, Jr. ............ 137/625.42
(Continued)

FOREIGN PATENT DOCUMENTS

DE 35 03 044 7/1986
(Continued)

OTHER PUBLICATIONS

European Search Report from the corresponding EP 02 78 0067, mailed Mar. 26, 2007.
(Continued)

*Primary Examiner*—Leslie R Deak
*Assistant Examiner*—Adam Marcetich
(74) *Attorney, Agent, or Firm*—Hamre, Schumann, Mueller & Larson, P.C.

(57) ABSTRACT

A three-way stopcock that can be opened/closed in the same manner as conventional operation methods and can reduce stagnated portions of fluid in a fluid flow passage. Out of branch openings, a first branch opening and a second branch opening are arranged on a straight line, and a third branch opening is directed perpendicularly to the line connecting the first and second branch openings. Provided at a flow passage switch portion are a first flow-passage opening and a second flow-passage opening that are arranged on a straight line and a third flow-passage opening that is directed perpendicularly to the line connecting the first and second bran openings.

10 Claims, 11 Drawing Sheets

U.S. PATENT DOCUMENTS

| | | | | |
|---|---|---|---|---|
| 3,481,367 | A | * | 12/1969 | Deuschle ............... 137/625.47 |
| 3,957,082 | A | * | 5/1976 | Fuson et al. ........... 137/625.41 |
| 4,197,876 | A | * | 4/1980 | Lobdell ................ 137/625.47 |
| 4,314,586 | A | * | 2/1982 | Folkman ................ 137/625.47 |
| 4,593,717 | A | * | 6/1986 | Levasseur ................ 137/556.6 |
| 5,084,031 | A | * | 1/1992 | Todd et al. ................... 604/248 |
| 5,104,387 | A | * | 4/1992 | Pokorney et al. ............ 604/248 |
| 5,228,646 | A | * | 7/1993 | Raines ........................ 251/95 |
| 5,443,453 | A | * | 8/1995 | Walker et al. ............... 604/248 |
| 5,466,228 | A | | 11/1995 | Evans |
| 5,478,537 | A | * | 12/1995 | Laughlin et al. ............ 422/266 |
| 5,540,668 | A | * | 7/1996 | Wilson et al. ............... 604/248 |
| 5,839,470 | A | * | 11/1998 | Hiejima et al. ......... 137/599.08 |
| 5,916,201 | A | * | 6/1999 | Wilson et al. ............... 604/248 |
| 5,944,055 | A | * | 8/1999 | Dicky .................... 137/625.47 |
| 6,171,287 | B1 | * | 1/2001 | Lynn et al. ................... 604/256 |
| 6,418,966 | B2 | * | 7/2002 | Loo ....................... 137/625.47 |
| 6,626,884 | B1 | * | 9/2003 | Dillon et al. ................. 604/409 |
| 7,232,428 | B1 | * | 6/2007 | Inukai et al. ................. 604/248 |

FOREIGN PATENT DOCUMENTS

| | | |
|---|---|---|
| EP | 1 234 596 | 8/2002 |
| EP | 1 790 378 A | 5/2007 |
| JP | 2000-350787 A | 12/2000 |
| JP | 2001-190689 A | 7/2001 |
| JP | 2004-254789 A | 9/2004 |
| WO | WO 96/26760 | 9/1996 |
| WO | 01/39826 | 6/2001 |
| WO | WO 01/58507 A | 8/2001 |
| WO | WO 2004/101061 A | 11/2004 |
| WO | WO 2006/025054 A | 3/2006 |

OTHER PUBLICATIONS

Japanese Office Action for the corresponding JP application 2003-543673, mailed Oct. 24, 2006.

* cited by examiner

THREE-WAY STOPCOCK, AND LIQUID TRANSFUSION CIRCUIT OR BLOOD TRANSFUSION CIRCUIT EITHER USING THE THREE-WAY STOPCOCK

TECHNICAL FIELD

The present invention relates to a three-way stopcock capable of changing the route of a fluid flow passage by performing a rotational operation of a flow passage switching portion provided in a body having three branch openings so as to allow the communication between predetermined branch openings out of the three branch openings, and relates to a liquid transfusion tubing set or a blood transfusion tubing set using the same.

BACKGROUND ART

Figure 9:
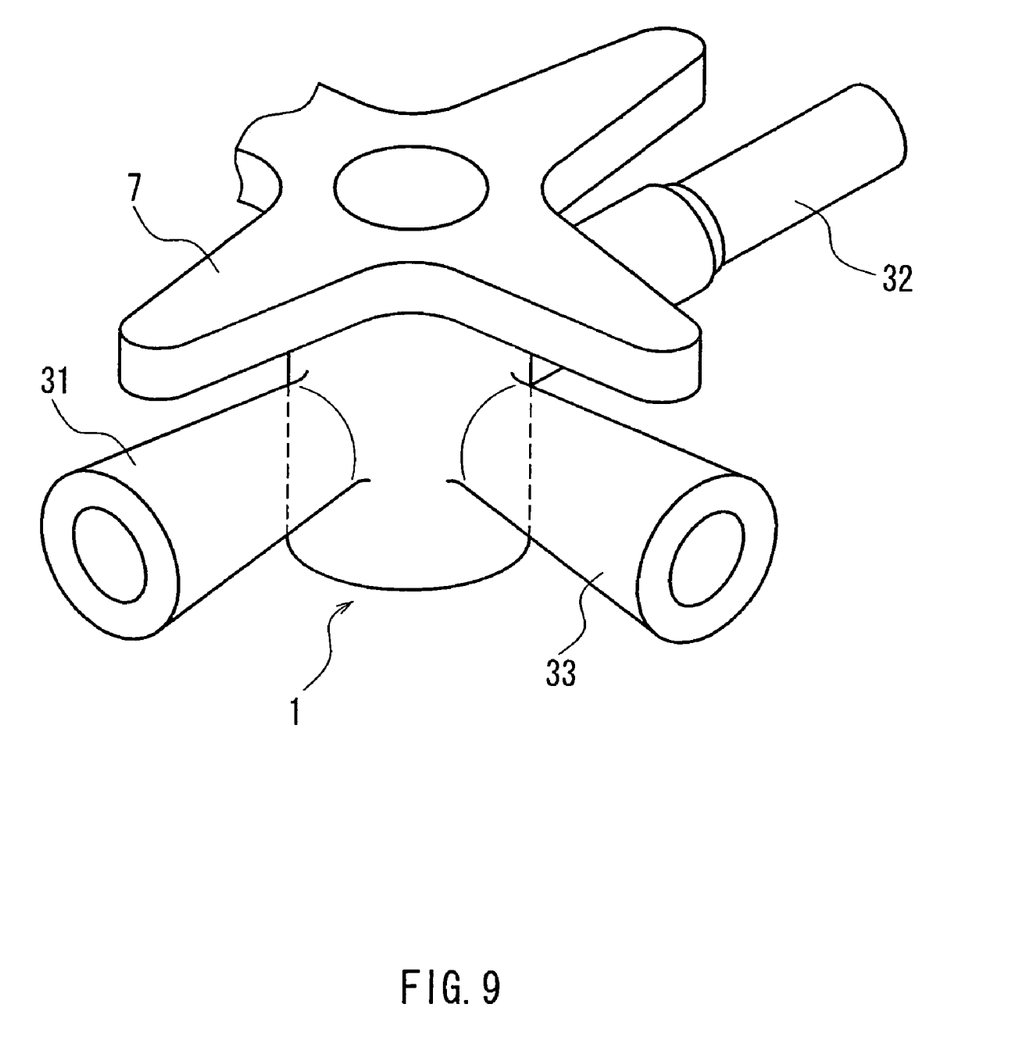
FIG. 9 is an overall perspective view of the conventional three-way stopcock.

When a medical treatment is conducted by liquid transfusion or blood transfusion in medical facilities, a three-way stopcock is used for carrying out mixture injection of different types of medical fluid and for taking a fluid flowing through a fluid flow passage. FIG. 9 shows an overall perspective view of a conventional three-way stopcock, in which the conventional three-way stopcock is configured with: a body 1 provided with branch pipes that are connected to three branch openings and in which a fluid can flow; and a flow passage switching portion 5. The conventional three-way stopcock is configured in a manner that a rotational operation of a handle 7 configured integrally with the flow passage switching portion 5 allows the selection of a combination of a branch pipe into which a medical fluid flows and a branch pipe communicating with the branch pipe so that the medical fluid flows out of there.

Out of the three branch pipes in the conventional three-way stopcock, a first branch pipe 31 and a second branch pipe 32 are arranged so as to assume a straight-line flow passage form when they communicate with each other. This flow passage is designated as a main line. In addition, a branch pipe that is arranged perpendicularly to the main line is a third branch pipe 33, through which mixture injection of medical fluids is carried out and a fluid is taken.

Figure 10:
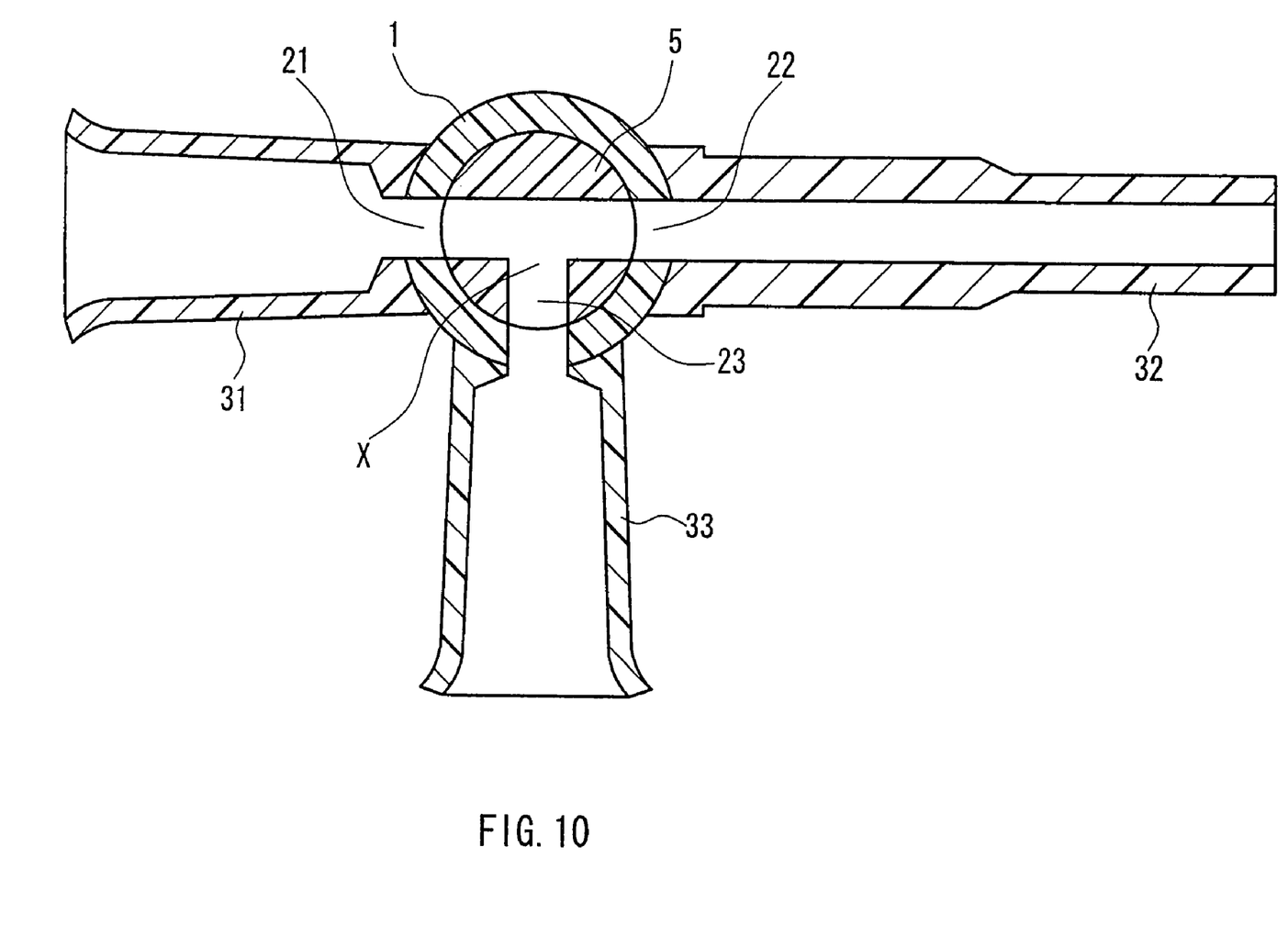
FIG. 10 is a transverse sectional view of the conventional three-way stopcock.

FIG. 10 is a transverse sectional view of the conventional three-way stopcock. As shown in FIG. 10, the body 1 is provided with the three branch openings 21, 22 and 23 so as to allow the selectable combination of the first branch pipe 31, the second branch pipe 32 and the third branch pipe 33.

Figure 11:
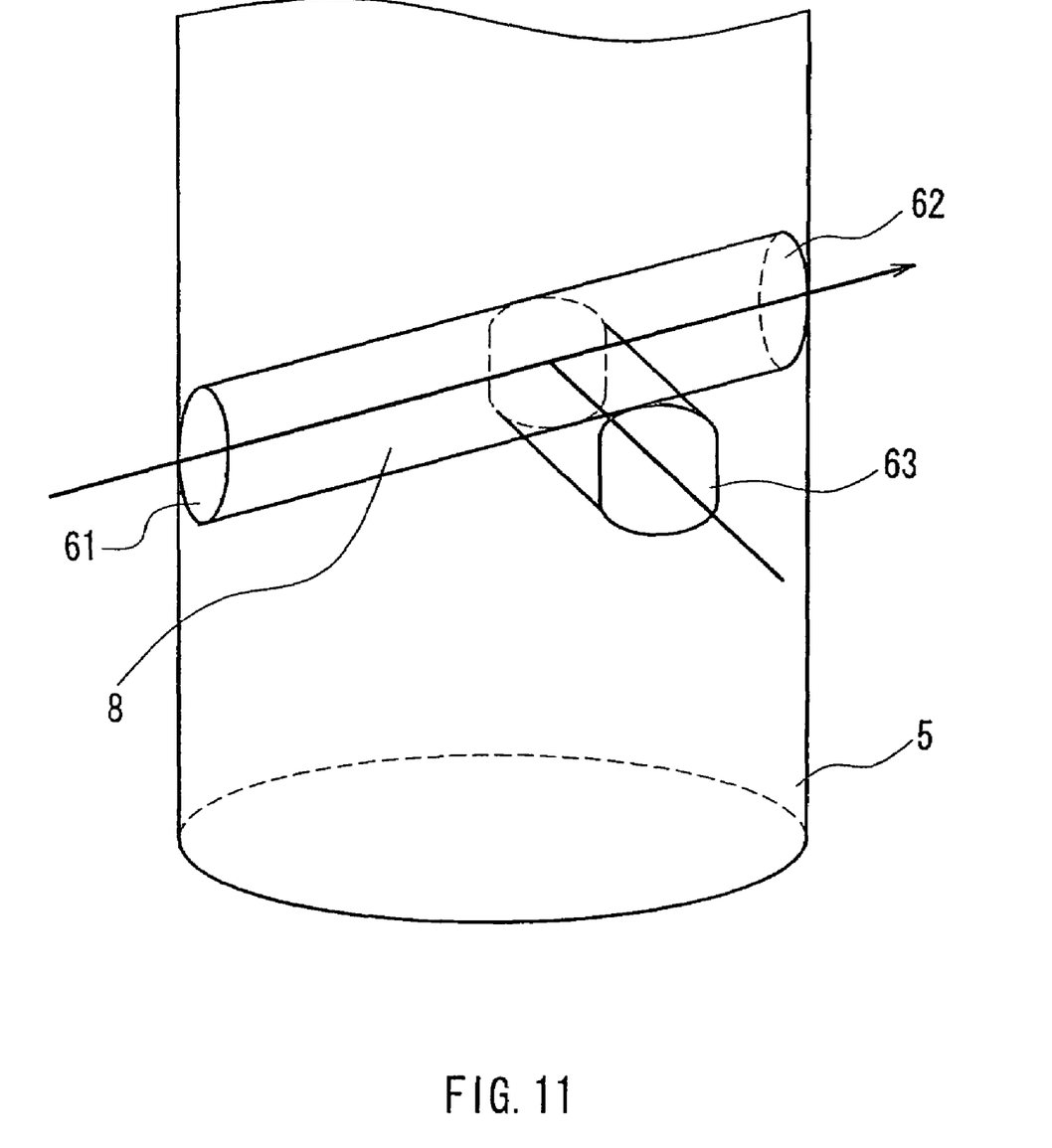
FIG. 11 schematically shows the direction of a flow passage in the flow passage switching portion of the conventional three-way stopcock.

FIG. 11 schematically shows the direction of a flow passage in the flow passage switching portion of the conventional three-way stopcock. As shown in FIG. 11, the flow passage switching portion 5 is provided with three flow passage openings 61, 62 and 63. In addition, a fluid flow passage 8 provided in the flow passage switching portion 5 is configured with a flow passage through which the first flow passage opening 61 and the second flow passage opening 62 communicate with each other in a straight line and a flow passage that is arranged so as to branch perpendicularly from the center of this flow passage so as to communicate with the third flow passage opening 63. In other words, the fluid flow passage 8 is configured in the shape of a T.

The third branch pipe 33, however, might be opened to the outside during the mixture injection, resulting in the possibility that bacteria get into there. That is to say, as the third branch pipe 33 has a hollow and long-size pipe structure and it is difficult to disinfect the long-size bore of the pipe, there is the risk that the bore in the third branch pipe 33 becomes a breeding ground for bacteria.

Furthermore, since the flow passage switching portion 5 is configured, as shown in FIG. 10, in the shape of a T with a portion branching partway, there is the risk that the flow of the main line does not affect the portion X in the flow passage that communicates with the third flow passage opening 63, resulting in the generation of a stagnated portion. Due to the presence of the stagnated portion, a medical fluid to be given might remain there, which causes a problem that it becomes difficult to administer the medical fluid precisely.

Meanwhile, in the recent medical scenes, as an insertion member for mixture injection equipment such as an injection needle for use in mixture injection, a specially designed blunt needle is used instead of a sharp metal needle.

Correspondingly, various three-way stopcocks have been developed, as disclosed in JP 11(1999)-342209 A, in which a septum of an elastic member having a slit through which a blunt needle can be punctured is provided at a position corresponding to the third branch pipe for the purpose of eliminating the stagnated portion in the third branch pipe 33. The three-way stopcock disclosed in JP 11(1999)-342209 A is a medical stopcock having a feature in which an arcuate groove-like switching passage is formed along the circumferential surface at the switching portion of the flow passage. In this three-way stopcock, the septum of an elastic member having the slit is disposed at the position corresponding to the third branch pipe 33, so that the branch pipe is isolated from the outside so as to secure a closed system and at the same time the length of the flow passage can be shortened relative to the conventional one. In addition, by forming the arcuate groove-like switching passage along the circumferential surface at the switching portion of the flow passage, a flow of the fluid is generated also at the portion conventionally acting as the stagnated portion, so as to eliminate the stagnated portion.

These three-way stopcocks, however, have a drawback in that a closing of all of the flow passages cannot be made by adopting a method in which an angular position of the fluid flow passage is shifted slightly, which is a normal method in the conventional three-way stopcocks. That is to say, there is a problem in that it is not possible to close all of the flow passages by rotating the flow passage switching portion 5 from the state of FIG. 10 to a state corresponding to an intermediate angular position within an angle made by the position of the third branch pipe 33 and the position of the first branch pipe 31 or the second branch pipe 32 (45° or 315°) as in the conventional methods.

For example, in the three-way stopcock disclosed in JP 11(1999)-342209 A, when all of the flow passages are closed, the fluid switching portion 5 should be rotated by about 135° to 225°. This results from the fact that, while the flow passage switching portion 5 in the conventional three-way stopcocks has three openings, this flow passage switching portion 5 has an arcuate groove form along the circumferential surface, which means the opening portion is open to a large degree. In the practical medical scenes, in particular, complicated operations should be done securely in a short time, and therefore the three-way stopcock having such a configuration has the possibility of operating errors occurring during the use thereof.

DISCLOSURE OF THE INVENTION

In view of the above-stated circumstances, an object of the present invention is to provide a three-way stopcock that can reduce a stagnated portion of a fluid in a fluid flow passage and can be opened/closed in the same manner as the conventional operation methods.

In order to fulfill the above-stated object, a three-way stopcock according to the present invention includes: a substantially cylindrical shaped body having three branch openings on a periphery thereof, and a flow passage switching portion that is mounted to the body so as to be rotatable with respect to the body and to have liquid-tightness, and has three flow passage openings that form fluid flow passages so as to allow communication between predetermined branch openings out of the respective three branch openings, wherein the fluid flow passages can be changed by rotating the flow passage switching portion with respect to the body. Out of the branch openings, a first branch opening and a second branch opening are formed on a straight line, and a third branch opening is arranged in a direction perpendicular to the straight line connecting the first branch opening and the second branch opening. The flow passage switching portion is provided with a first flow passage opening and a second flow passage opening that are formed on a straight line and a third flow passage opening arranged in a direction perpendicular to the straight line connecting the first flow passage opening and the second flow passage opening. The flow passage switching portion is provided with two fluid flow passages, each connecting the first flow passage opening to the third flow passage opening and the third flow passage opening to the second flow passage opening, the two fluid flow passages being formed so as to allow communication with each other in the vicinity of the third flow passage opening.

With this configuration, the three flow passage openings are provided so as to be open to the flow passage switching portion, and the two fluid flow passages connecting the respective flow passage openings are formed to be capable of communicating with each other. Therefore, the flow of a fluid can reach a space in the branch opening also, and by performing the priming or the like, a stagnated portion of the fluid can be eliminated.

Furthermore, the opening portions of the flow passage switching portion are only the three flow passage openings. Therefore by adjusting the portions of the flow passage switching portion having none of the three flow passage openings to the positions of the respective branch openings of the body, the state where the flow passage openings do not communicate with the respective branch openings can be realized. Accordingly, the same operation method as in the conventional three-way stopcocks can be realized.

In addition, in the three-way stopcock according to the present invention, it is preferable that the third flow passage opening is formed with two flow passage openings, one of which communicates with the first flow passage opening and the other of which communicates with the second flow passage opening, and at a side wall portion where the two flow passage openings are formed in the third flow passage opening, a groove portion is provided so as to allow communication between the two fluid flow passages. Even in the case where a space is not formed in the branch opening due to a difference in the type of the injection port, a stagnated portion of the fluid can be eliminated by conducting the priming or the like.

In addition, in the three-way stopcock according to the present invention, it is preferable that the two flow passage openings in the third flow passage opening are provided to be arranged in a vertical direction of the body. This configuration can reduce the degree of the shift in an angular position when making the portions of the flow passage switching portion having none of the three flow passage openings face the respective branch openings of the body.

In addition, in the three-way stopcock according to the present invention, it is preferable that an injection port is provided at a side wall portion that forms the third branch opening. Furthermore, it is preferable that the injection port is capable of being inserted with an insertion member having a blunt tip and is capable of maintaining liquid-tightness.

In addition, in the three-way stopcock according to the present invention, it is preferable that a ratio of a cross-sectional area of the fluid flow passages with respect to a cross-sectional area of the third branch opening is 1:49 or more. Furthermore, it is preferable that a ratio of a cross-sectional area of the fluid flow passages with respect to a cross-sectional area of the third branch opening is 1:12.25 or more. In the case of the ratio being smaller than 1:49, the diameter of the fluid flow passages becomes too small to pass a fluid having a relatively high fluid viscosity, such as blood, which is unusable for practical applications. In the case of the ratio being 1:12.25 or more, it was confirmed by an experiment that a stagnated portion does not occur after the priming.

By making up a liquid transfusion tubing set and a blood transfusion tubing set using the above-stated three-way stopcocks, the same effects can be expected in such a liquid transfusion tubing set and a blood transfusion tubing set also.

Note here that a "vertical direction" used in the three-way stopcocks described in this specification is defined as a positional relationship of the three-way stopcock assuming that a handle provided in the flow passage switching portion is set at the uppermost part and other end portions are set at the lowermost part, that is, as a direction in a rotational axis of the flow passage switching portion. A "horizontal direction" is defined as a positional relationship in the direction perpendicular to the "vertical direction".

BEST MODE FOR CARRYING OUT THE INVENTION

The following describes a three-way stopcock according to embodiments of the present invention in detail, with reference to the attached drawings.

Figure 1:
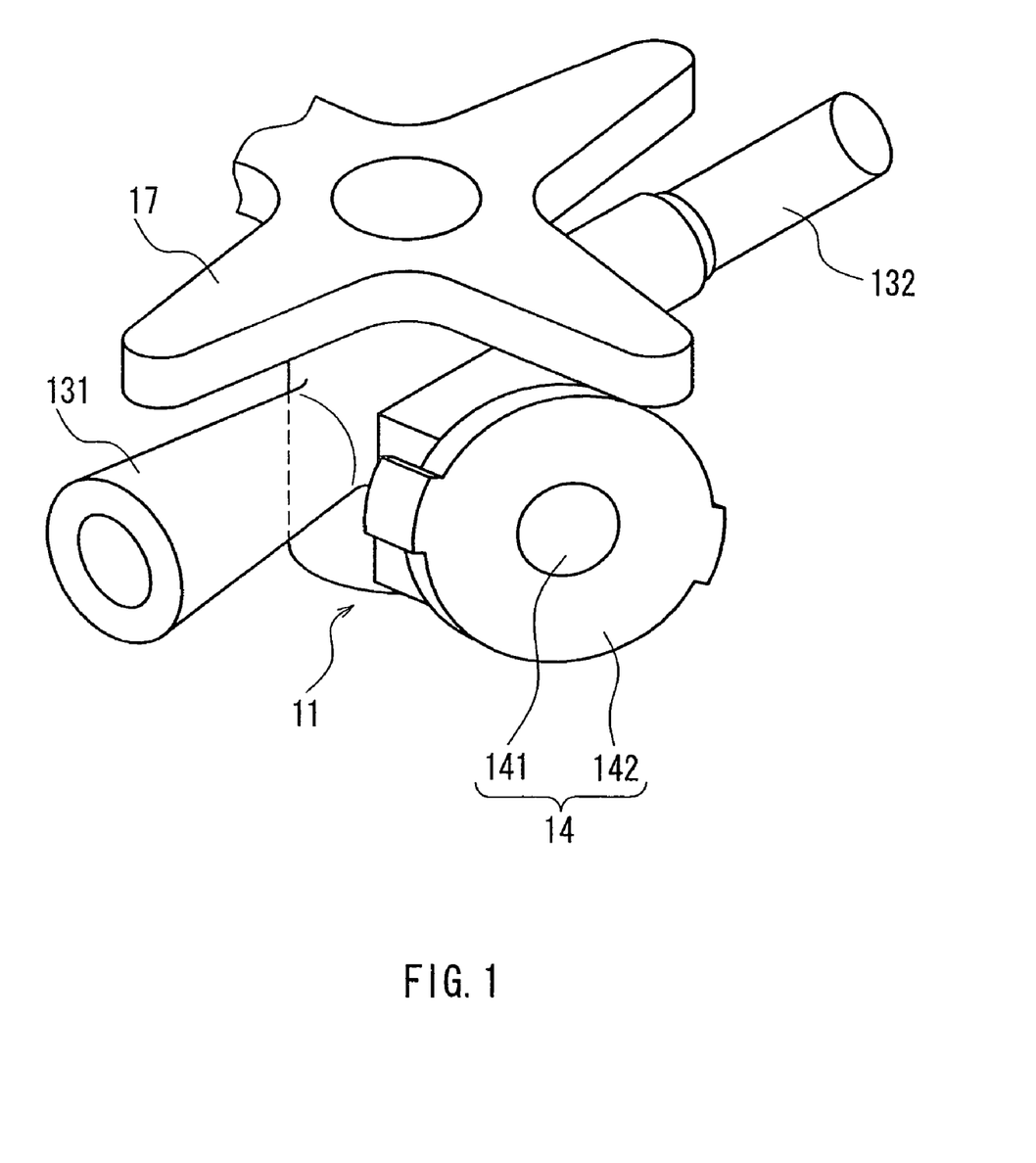
FIG. 1 is an overall perspective view of a three-way stopcock according to an embodiment of the present invention.

First, FIG. 1 is a perspective view of a three-way stopcock according to an embodiment of the present invention. The three-way stopcock according to the embodiment of the present invention is configured with a substantially cylindrical-shaped body 11 having three branch openings on the periphery thereof and a flow passage switching portion. The flow passage switching portion is mounted so as to be rotatable relative to the body 11 and provide fluid-tightness, has three flow passage openings that form a fluid flow passage so as to allow the communication between predetermined branch openings out of the respective branch openings of the body 11 and is configured integrally with a handle 17.

Figure 2:
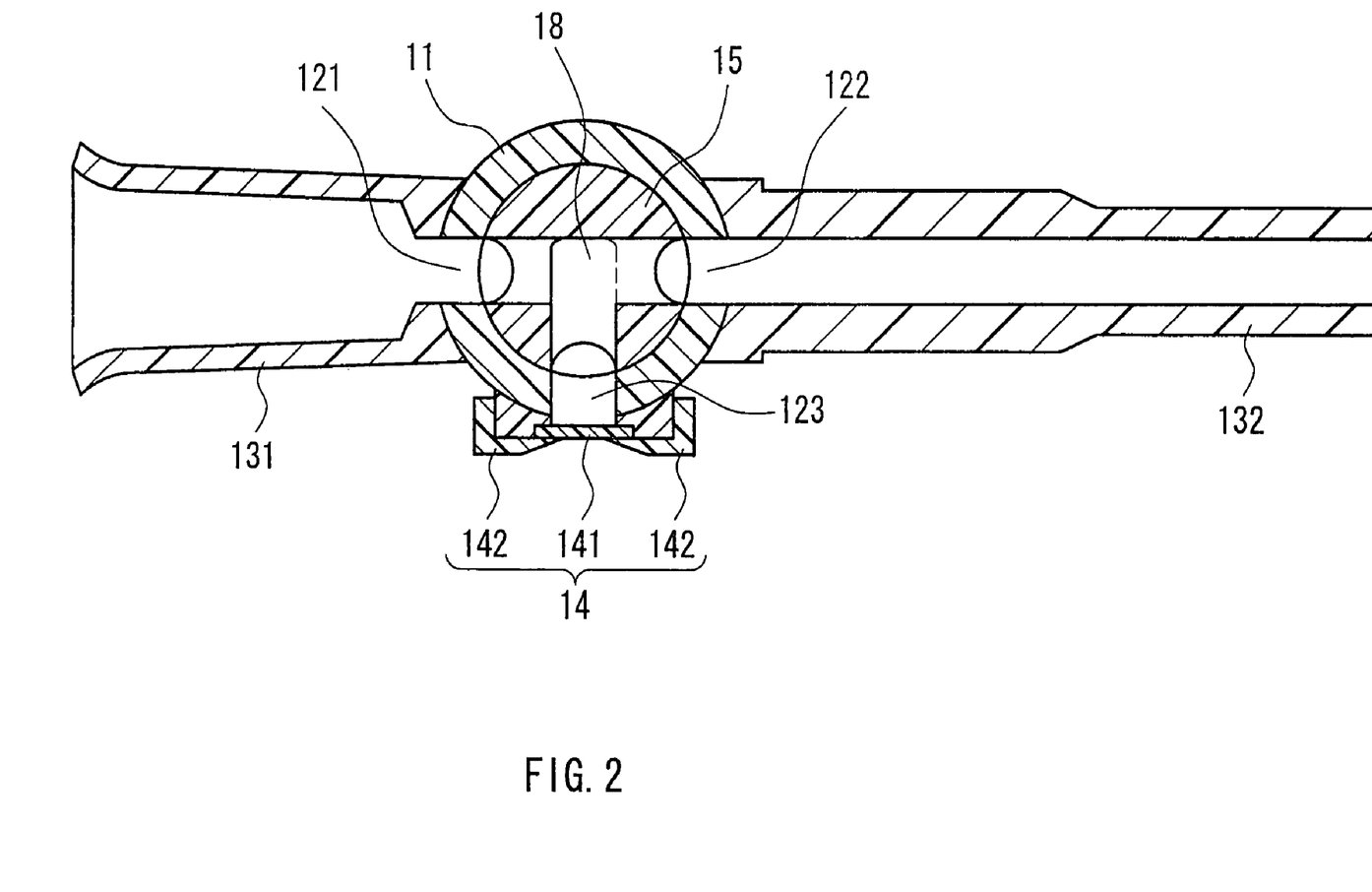
FIG. 2 is a transverse sectional view of the three-way stopcock according to the embodiment of the present invention.

FIG. 2 is a transverse sectional view of the three-way stopcock according to the embodiment of the present invention. As shown in FIG. 2, in the body 11, the three branch openings 121, 122 and 123 are formed. The first branch opening 121 and the second branch opening 122 are formed at opposed positions on the periphery of the body 11, and the third branch opening 123 is on the periphery of the body 11 and at a position that equally divides the angle between the first branch opening 121 and the second branch opening 122 into 90°. In addition, a first branch pipe 131 and a second branch pipe 132 respectively are connected to the first branch opening 121 and the second branch opening 122 so as to introduce a fluid into/from there.

Meanwhile, an injection port 14 is connected to the third branch opening 123. The injection port 14 is provided with a septum 141 through which a needle or the like can be punctured and is provided for isolating a fluid flow passage 18 in the three-way stopcock from the outside. The injection port 14 is configured in a manner that the septum 141 is fixed by a cover 142 so that an insertion portion only is exposed. With this configuration, a closed system to the outside can be formed securely in the fluid flow passage 18 within the three-way stopcock.

Note here that as to the injection port 14 used in the three-way stopcock according to the present invention, any mode of well-known injection ports can be used. The septum 141 may have a configuration capable of being punctured with a needle or the like and of maintaining a closed system of the fluid flow passage after removing the needle. In addition, the septum 141 may have a configuration provided with a slit beforehand so as to facilitate the puncturing of a needle or the like and ensure liquid-tightness. Moreover, the septum 141 may have a configuration through which an insertion member having a blunt tip such as a luer can be inserted and so as to ensure liquid-tightness.

Figure 3:
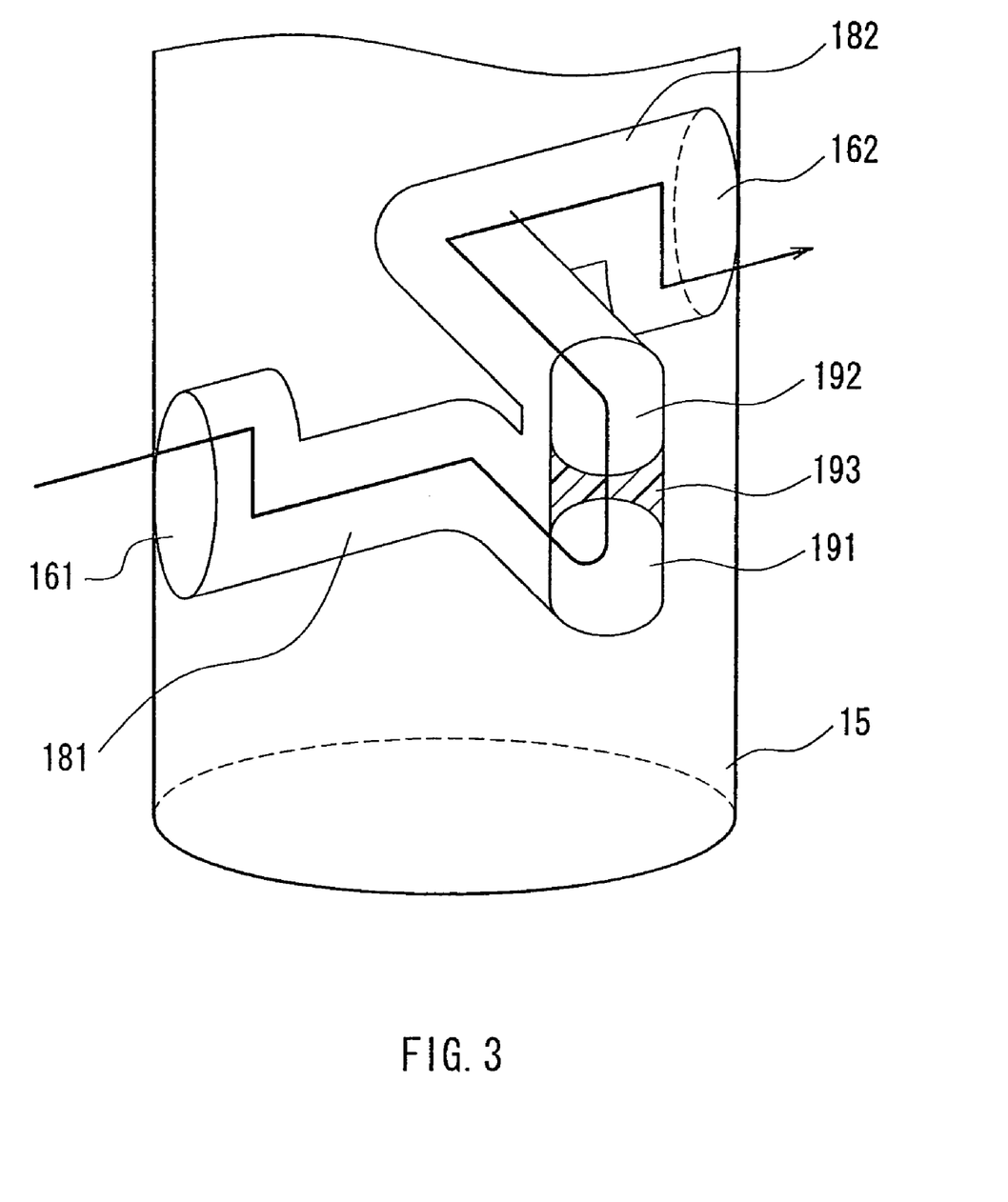
FIG. 3 schematically shows the direction of a flow passage in the flow passage switching portion of the three-way stopcock according to the embodiment of the present invention.

In addition, the flow passage switching portion 15 is rotatable in the body 11 and is mounted thereto so as to provide liquid-tightness. FIG. 3 schematically shows the direction of a flow passage in the flow passage switching portion 15 of the three-way stopcock according to the embodiment of the present invention. In FIG. 3, the arrow indicates the direction of a flow of the fluid.

In the flow passage switching portion 15, three flow passage openings 161, 162 and 163 are formed. The first flow passage opening 161 and the second flow passage opening 162 are formed at opposed positions on the periphery of the flow passage switching portion 15, and the third flow passage opening 163 is on the periphery of the flow passage switching portion 15 and at a position that equally divides the angle between the first flow passage opening 161 and the second flow passage opening 162 into 90°.

In addition, the fluid flow passage 18 provided in the flow passage switching portion 15 is configured with a first fluid flow passage 181 establishing the communication between the first flow passage opening 161 and the third flow passage opening 163 and a second fluid flow passage 182 establishing the communication between the second flow passage opening 162 and the third flow passage opening 163. Furthermore, the first fluid flow passage 181 and the second fluid flow passage 182 are provided so as to communicate with each other in the vicinity of the third flow passage opening 163.

As a means for enabling the communication between the first fluid flow passage 181 and the second fluid flow passage 182 in the vicinity of the third flow passage opening 163, various means can be considered. For example, as shown in FIG. 3, it can be considered as an effective means to provide a groove portion 193 (the diagonally shaded area in FIG. 3) between a base portion 191 of the first fluid flow passage 181 and a base portion 192 of the second fluid flow passage 182 within the third flow passage opening 163.

In addition, the base portions 191 and 192 of the first fluid flow passage 181 and the second fluid flow passage 182 are provided at the third flow passage opening 163 so that the base portion 191 of the first fluid flow passage 181 establishing the communication between the first flow passage opening 161 and the third flow passage opening 163 is located on the lower side and the base portion 192 of the second fluid flow passage 182 establishing the communication between the second flow passage opening 162 and the third flow passage opening 163 is located on the upper side in the vertical direction of the body 11 of the three-way stopcock.

Figure 4:
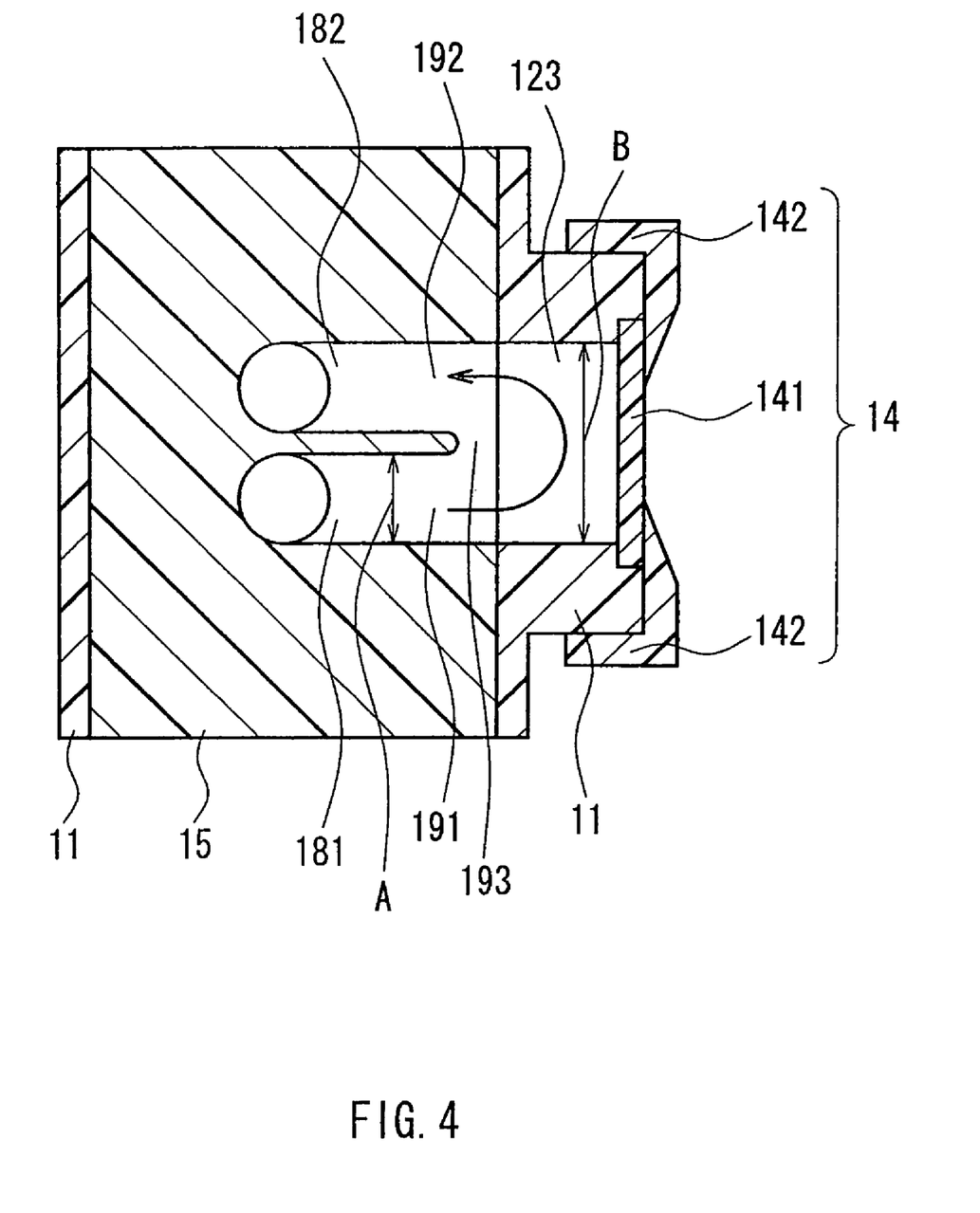
FIG. 4 is a vertical sectional view of the flow passage switching portion of the three-way stopcock according to the embodiment of the present invention.

FIG. 4 is a vertical sectional view of the state in which the flow passage switching portion 15 is rotated so that this third flow passage opening 163 coincides with the third branch opening 123 provided with the injection port 14 having the septum 141.

As shown in FIG. 4, a fluid introduced from the first fluid flow passage 181 changes its direction at the third branch opening 123 by passing through a space formed by the groove portion 193 and the third branch opening 123, so as to flow toward the second fluid flow passage 182 located on the upper side. At this time, the fluid flows while circulating through the space formed in the third branch opening 123 in the body 11, thus preventing that space from acting as a stagnated portion of the fluid.

At this time, in order to let the fluid flow so as to circulate through the space in the third branch opening 123, larger cross-sectional areas of the first fluid flow passage 181 and the second fluid flow passage 182 lead to more effective flow with circulation. However, since the first fluid flow passage 181 and the second fluid flow passage 182 have to be present within the area of the third branch opening 123, the cross-sectional area A of the first fluid flow passage 181 and the second fluid flow passage 182 does not become larger with respect to the cross-sectional area B of the third branch opening 123 than a ratio of 1:2.

On the other hand, when the cross-sectional area A of the first fluid flow passage 181 and the second fluid flow passage 182 is decreased, it becomes difficult to secure a flow rate of the three-way stopcock and to perform a function as a fluid flow passage for a fluid having a high viscosity.

Figure 5:
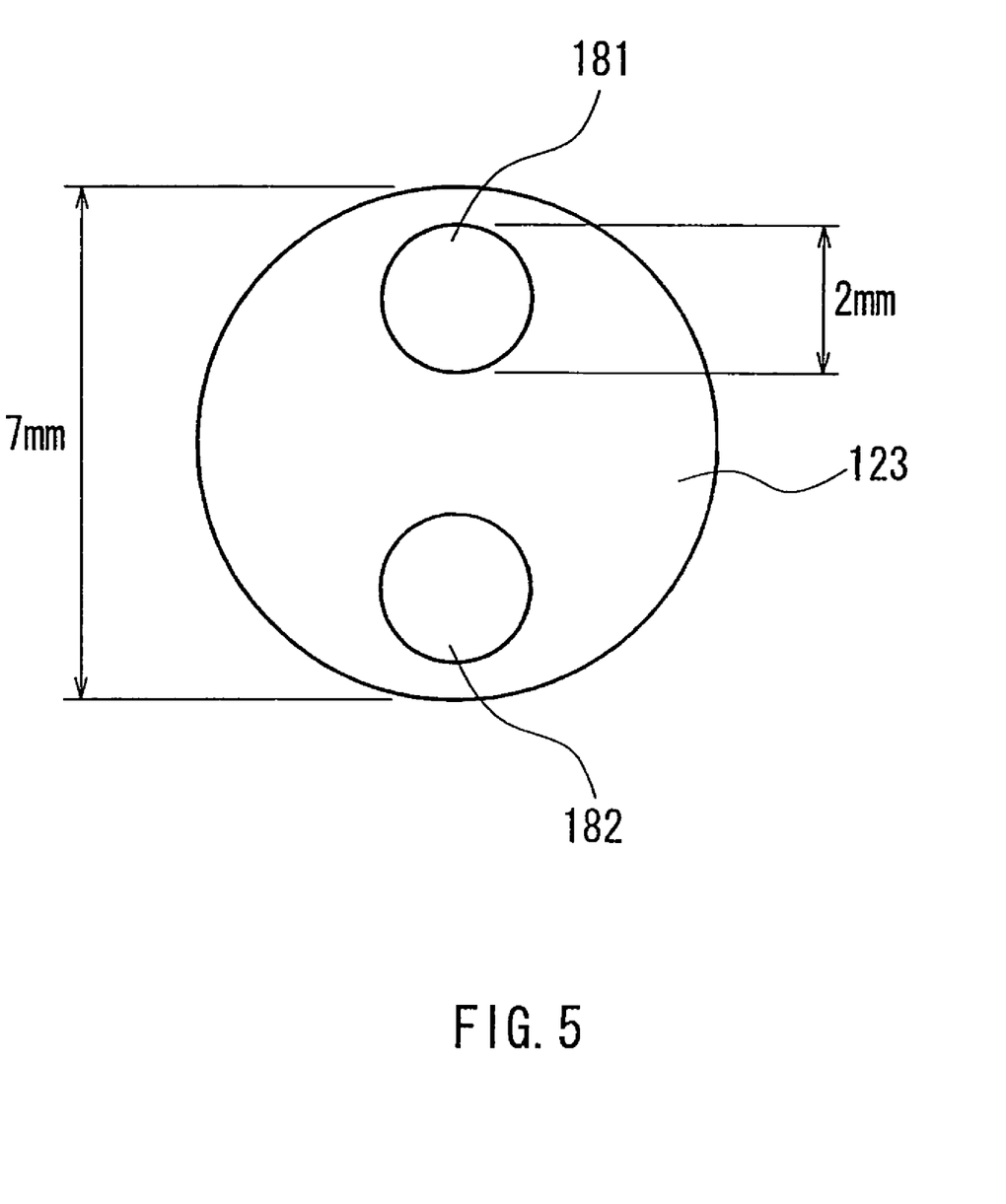
FIG. 5 is a front view of a third branch opening in the three-way stopcock according to the embodiment of the present invention.

An experiment was conducted with a configuration as shown in FIG. 5, in which the first fluid flow passage 181 and the second fluid flow passage 182 were formed in the third branch opening 123. Impurities were injected in the space in the third branch opening 123, and then a density of the residual impurities after the priming operation was measured so as to determine whether the space formed in the third branch opening 123 acted as a stagnated portion of the fluid or not.

As a result, in the configuration shown in FIG. 5, no impurities remained. As long as the cross-sectional area A of the first fluid flow passage 181 and the second fluid flow passage 182 satisfies an area ratio of 1:12.25 or more with respect to the cross-sectional area B of the third branch opening 123, a stagnated portion of the fluid does not occur.

Meanwhile, in terms of the manufacturing process, it is difficult to make diameters of the first fluid flow passage 181 and the second fluid flow passage 182 smaller than 1 mm. In addition, if the diameters of the first fluid flow passage 181 and the second fluid flow passage 182 become smaller than 1 mm, in the case of liquid having a relatively high fluid viscosity, such as blood, there is the empirically evident fact that the clogging becomes likely to occur, thus inhibiting the fluent flow. Therefore, it is desirable that the cross-sectional area A of the first fluid flow passage 181 and the second fluid flow passage 182 satisfies an area ratio of 1:49 or more with respect to the cross-sectional area B in the third branch opening 123.

In addition, it can be considered that, depending on the configuration of the injection port 14, there is no space of the third branch opening 123. However, in this case also, a fluid introduced from the first fluid flow passage 181 changes its direction by passing through the groove portion 193 at the third branch opening 123, so as to flow toward the second fluid flow passage 182 that is located on the upper side.

Meanwhile, the first fluid flow passage 181 and the second fluid flow passage 182 have the base portions 191 and 192, respectively, facing at the third flow passage opening 163, extend toward the center of the flow passage switching portion 15 while keeping the respective vertical positional relationship, and are bent at the center so as to extend toward the first flow passage opening 161 and the second flow passage opening 162, respectively.

With this configuration, the fluid flow passage in the flow passage switching portion 15 establishes the communication from the first flow passage opening 161 to the third flow passage opening 163 and the communication from the third flow passage opening 163 to the second flow passage opening 162, and is open at only three positions including the first flow passage opening 161, the second flow passage opening 162 and the third flow passage opening 163, which are the same as the opening positions of the flow passage switching portion in the conventional three-way stopcock.

Accordingly, in order not to have the flow passage openings communicate with the respective branch openings, the peripheral portions of the flow passage switching portion 15 having no flow passage opening are adjusted to face the respective branch openings of the body 11.

Note here that, at the third flow passage opening 163, the base portion 191 of the first fluid flow passage 181 communicating with the first flow passage opening 161 and the base portion 192 of the second fluid flow passage 182 communicating with the second flow passage opening 162 are provided so as to have the vertical positional relationship in the vertical direction of the body 11, which means that the two fluid flow passages communicate with each other in the vertical direction at the third flow passage opening 163.

The positions where the base portion 191 and the base portion 192 are arranged are not limited to this, and, for example, they may be provided horizontally in the lateral direction of the body 11.

However, the structure where the two fluid flow passages communicate with each other in the vertical direction at the third flow passage opening 163 makes it possible to shorten the length (length in the horizontal direction) of the third flow passage opening 163 along the periphery of the flow passage switching portion 15 as compared with the case of the two fluid flow passages communicating in the horizontal direction. Accordingly, the opening portion along the periphery of the flow passage switching portion 15 can be made smaller, so that a larger area on the periphery of the flow passage switching portion 15 having no opening portion can be kept, which enables the closing of all of the flow passages without significantly rotating the flow passage switching portion 15 with respect to the body 11 so as not to allow the flow passage openings communicate with the respective branch openings. That is to say, by adjusting the portions on the flow passage switching portion 15 having none of the three flow passage openings to the positions of the respective branch openings of the body 11, all of the branch openings can be closed.

In order to change the communicating state into the not-communicating state (closed state), the flow passage switching portion 15 has to be rotated. If a number of opening portions arranged in the horizontal direction is large, then a larger amount of shift in the angular position will be required. On the other hand, if a number of opening portions in the horizontal direction is small, then the change into the not-communicating state (closed state) can be conducted by a very small amount of shift in the angular position.

This embodiment is described for the case where, at the third flow passage opening 163, the base portion 191 of the first fluid flow passage 181 communicating with the first flow passage opening 161 and the base portion 192 of the second fluid flow passage 182 communicating with the second flow passage opening 162 have the positional relationship that the base portion 191 of the first fluid flow passage 181 is provided on a lower side and the base portion 192 of the second fluid flow passage 182 is provided on an upper side. However, even when their positional relationship in the vertical direction is reversed, the same effects can be expected.

Moreover, the configuration of the fluid flow passage in the flow passage switching portion 15 is not limited to the above-stated configuration. For example, as shown in FIG. 6, one possible configuration is that a first fluid flow passage 181 and a second fluid flow passage 182 having base portions 191 and 192, respectively, at a third flow passage opening 163 extend in a straight line toward a first flow passage opening 161 and a second flow passage opening 162, respectively, from the third flow passage opening 163.

Of course, the first fluid flow passage 181 and the second fluid flow passage 182 are provided so that they can communicate with each other in the vicinity of the third flow passage opening 163. As a means for allowing the communication between the first fluid flow passage 181 and the second fluid flow passage 182, possible one is to provide a groove portion 193 (the diagonally shaded area in FIG. 6) between the base portion 191 of the first fluid flow passage 181 and the base portion 192 of the second fluid flow passage 182 within the third flow passage opening 163 in the same manner as in FIG. 3.

Figure 6:
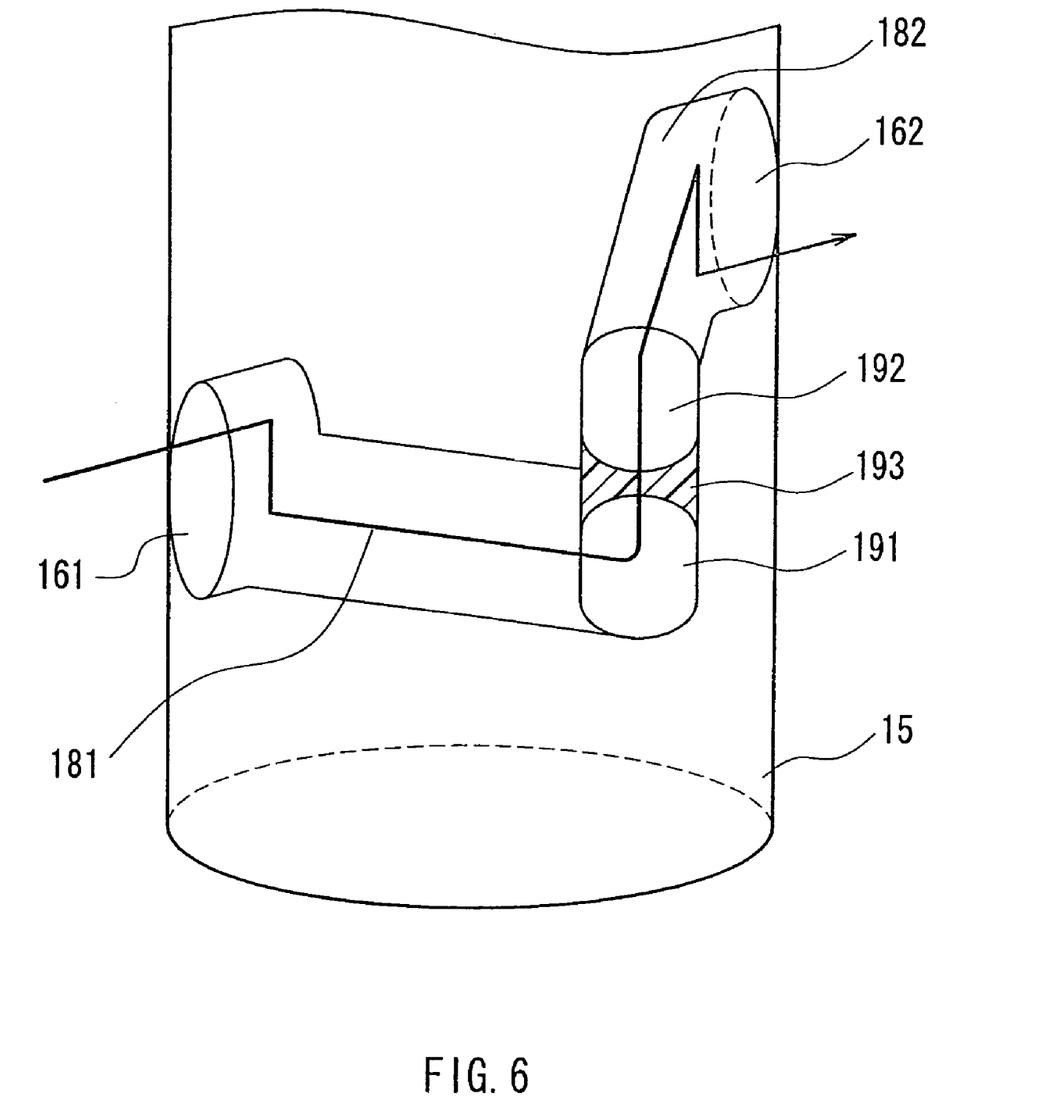
FIG. 6 schematically shows the direction of a flow passage in the flow passage switching portion of the three-way stopcock according to another embodiment of the present invention.
Figure 7:
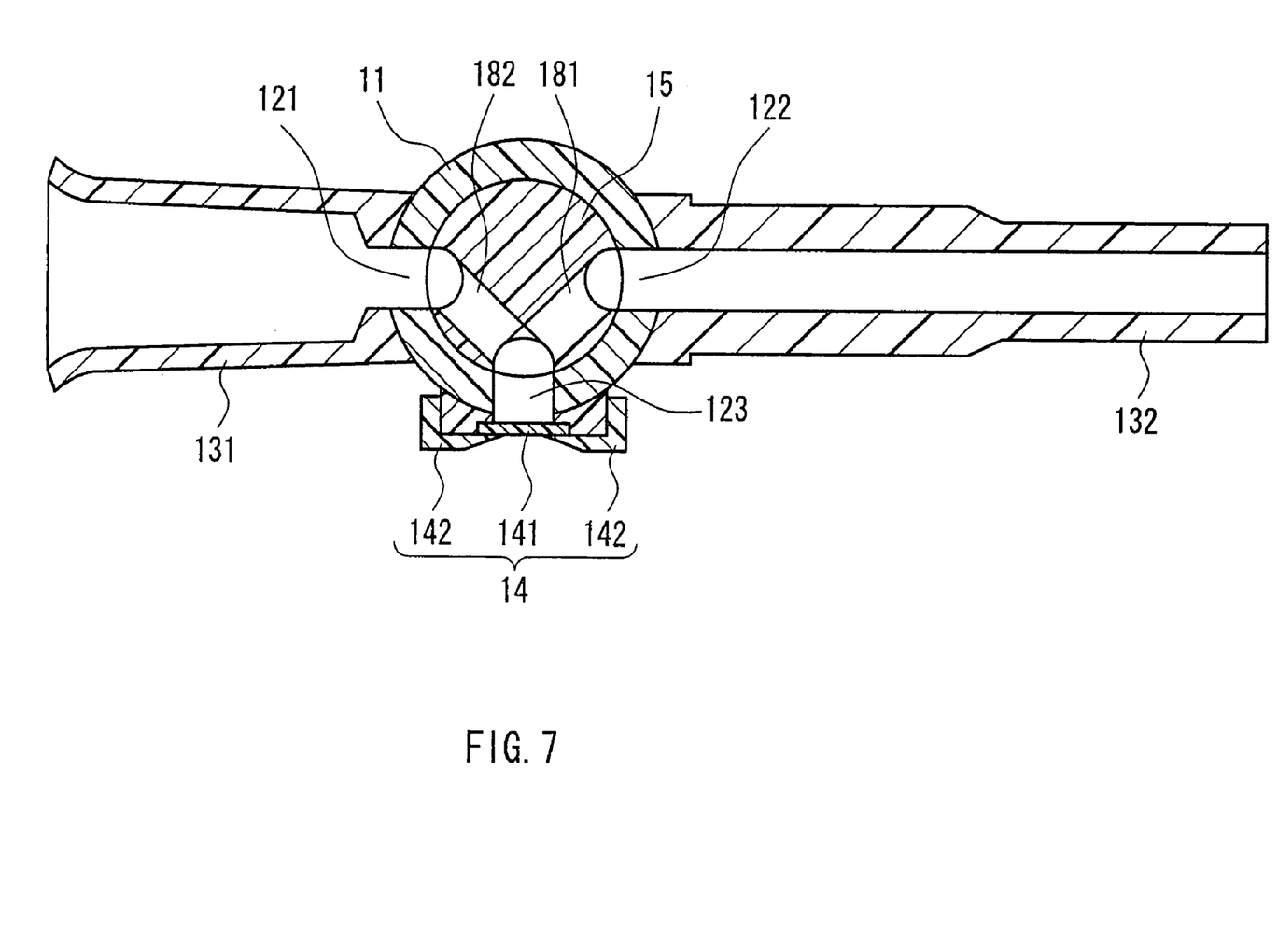
FIG. 7 is a transverse sectional view of the three-way stopcock according to the embodiment of the present invention.

FIG. 7 is a transverse sectional view of the flow passage switching portion 15 of FIG. 6, where a fluid flow passage formed within the flow passage switching portion 15 constitutes one fluid flow passage that flows from the first flow passage opening 161 to the second flow passage opening 162 through the third flow passage opening 163.

In such a configuration also, the openings of the flow passage switching portion 15 include only the first flow passage opening 161, the second flow passage opening 162 and the third flow passage opening 163 in the same manner as in the above-described embodiment, which is the same configuration of the openings of the flow passage switching portion of the conventional three-way stopcock, and therefore the same effects can be expected.

Figure 8:
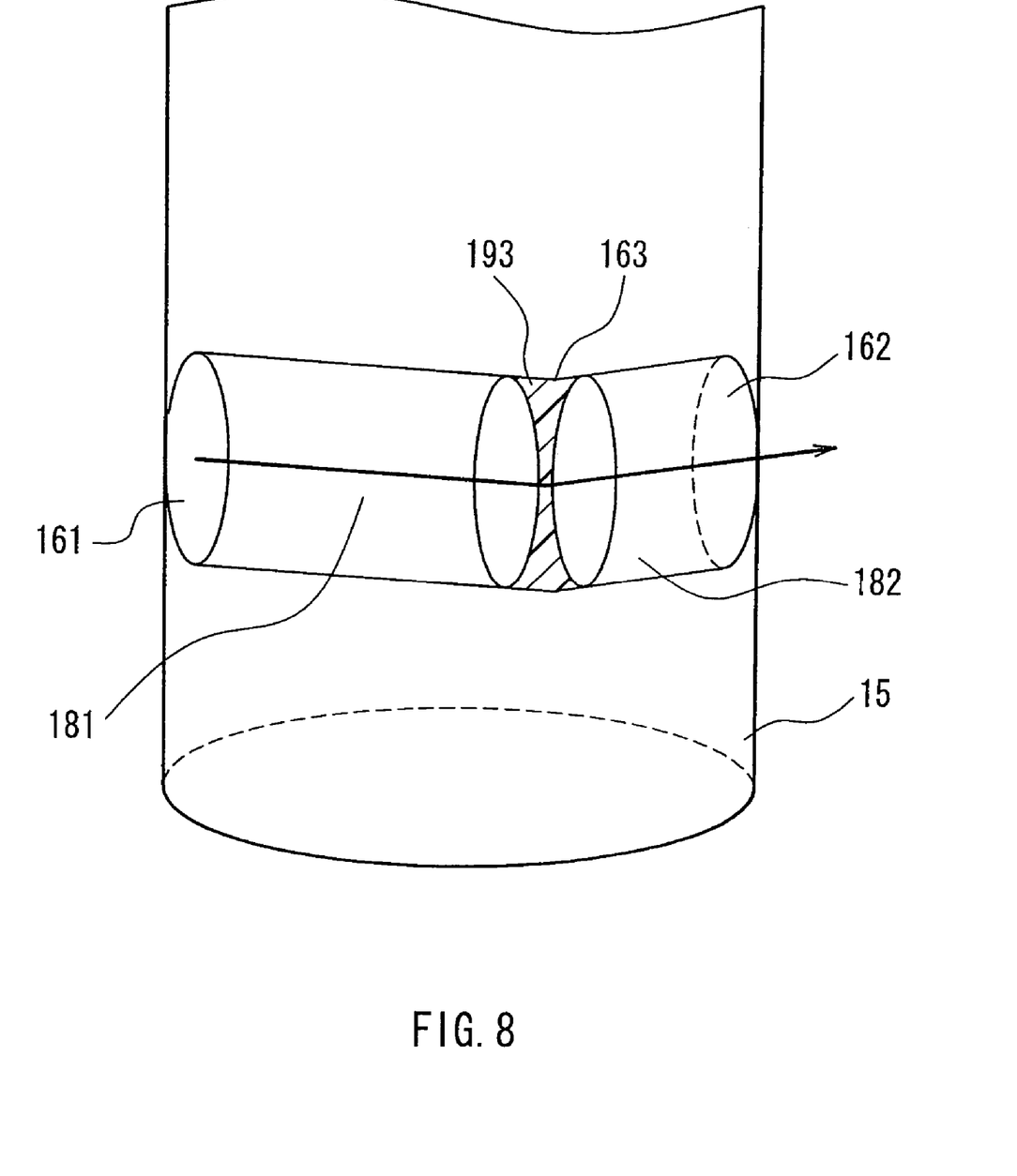
FIG. 8 schematically shows the direction of a flow passage in the flow passage switching portion of the three-way stopcock according to still another embodiment of the present invention.

Alternatively, as shown in FIG. 8, another configuration is such that a size of a third opening 163 is made equal to that of a first opening 161 and a second opening 162, and a first fluid flow passage 181 and a second fluid flow passage 182 extend in a straight line from a third flow passage opening. 163 to the first flow passage opening 161 and the second flow passage opening 162, respectively.

Of course, the first fluid flow passage 181 and the second fluid flow passage 182 are provided so that they can communicate with each other in the vicinity of the third flow passage opening 163. As a means for allowing the communication between the first fluid flow passage 181 and the second fluid flow passage 182, possible one is to provide a groove portion 193 (the diagonally shaded area in FIG. 8) between the base portion 191 of the first fluid flow passage 181 and the base portion 192 of the second fluid flow passage 182 within the third flow passage opening 163 in the same manner as in FIG. 3.

In such a configuration also, the openings of the flow passage switching portion 15 include only the first flow passage opening 161, the second flow passage opening 162 and the third flow passage opening 163 in the same manner as in the above-described embodiment, which is the same configuration of the openings of the flow passage switching portion of the conventional three-way stopcock, and therefore the same effects can be expected.

In addition, since the two fluid flow passages communicate at the third flow passage opening 163, there is no need to consider that the base portions of the fluid flow passages are positioned in the vertical direction or in the horizontal direction, and the like. Therefore, the opening portions on the periphery of the flow passage switching portion 15 can be reduced to the minimum. Therefore, in order to close all of the flow passages, the state where the flow passage openings do not communicate with the respective branch openings can be achieved without significantly rotating the flow passage switching portion 15 with respect to the body 11.

Note here that, as a material of the body of the three-way stopcock, normally, polycarbonate, polypropylene, polyacetal, acrylic resin, polycarbonate alloy or the like is used.

INDUSTRIAL APPLICABILITY

As stated above, according to the three-way stopcock of the present invention, as the fluid flow passages in the flow passage switching portion of the three-way stopcock are provided so as to communicate with each other at the injection port, the fluid flows so as to circulate through a space formed in the branch opening of the body, and therefore a stagnated portion does not occur in the space within the body. Thereby, a stagnated portion of the fluid can be eliminated in the three-way stopcock.

In addition, according to the three-way stopcock of the present invention, the respective openings can be provided at the similar positions to the conventional three-way stopcock, and therefore the three-way stopcock can be opened/closed in the same manner as in the conventional one. As a result, operating errors by medical staffs can be prevented before they happen.

The invention claimed is:

1. A three-way stopcock, comprising:

a substantially cylindrical shaped body having first through third branch openings on a periphery thereof, the first branch opening and the second branch opening being situated at respective opposite sides of a cylindrical periphery of the body and the third branch opening being situated between the first and second branch openings away therefrom at right angles; and a flow passage switching portion that is mounted in a cylindrical bore of the body so as to be rotatable around an axis of the cylindrical bore with respect to the body and to have liquid-tightness, and has flow passage bores that form fluid flow passages so as to allow communication between predetermined branch openings, wherein the fluid flow passages can be changed by rotating the flow passage switching portion with respect to the body, wherein the flow passage bores comprise a first flow passage bore for forming a first fluid flow passage from the first branch opening to the third branch opening and a second flow passage bore for forming a second fluid flow passage from the second branch opening to the third branch opening in a path separated from the first flow passage bore, both ends of the first and second flow passage bores form flow passage openings at a peripheral surface of the flow passage switching portion, the flow passage openings being separated from each other at the peripheral surface of the flow passage switching portion, two of the flow passage openings corresponding to the third branch opening are located adjacently and aligned along a direction parallel to the axis of the cylindrical bore, and when a relative angular position of the cylindrical body and the flow passage switching portion are set at a predetermined state, the first flow passage bore and the second flow passage bore are arranged to form the first fluid flow passage and the second fluid flow passage, respectively, at the same time, and the adjacent two flow passage openings confront the third branch opening.

2. The three-way stopcock according to claim 1, wherein on a peripheral surface of the flow passage switching portion, the respective fluid flow passage end openings corresponding to the third branch opening communicate with each other by passing around the periphery of a groove portion at the third branch opening.

3. The three-way stopcock according to claim 1, wherein an injection port is provided at a side wall portion that forms the third branch opening.

4. The three-way stopcock according to claim 3, wherein the injection port is capable of accepting an insertion member having a blunt tip and is capable of maintaining liquid-tightness.

5. The three-way stopcock according to claim 3, wherein a ratio of a cross-sectional area of either of the fluid flow passages with respect to a cross sectional area of the third branch opening is (1:49) or more.

6. The three-way stopcock according to claim 3, wherein a ratio of a cross-sectional area of either of the fluid flow passages with respect to a cross sectional area of the third branch opening is (1:12.25) or more.

7. A liquid transfusion tubing set that uses the three-way stopcock according to claim 1.

8. A blood transfusion tubing set that uses the three-way stopcock according to claim 1.

9. The three-way stopcock according to claim 1 wherein the first, second, and third branch openings are at a same horizontal plane of the cylindrical shaped body.

10. The three-way stopcock according to claim 1 wherein a first base portion of the first flow passage and a second base portion of the second flow passage extend in a straight line from the first flow passage opening and the second flow passage opening, respectively, to the third flow passage.

* * * * *